United States Patent
Plumere et al.

(10) Patent No.: US 9,187,779 B2
(45) Date of Patent: Nov. 17, 2015

(54) SYSTEMS AND METHODS FOR ENZYMATIC OXYGEN REMOVAL

(75) Inventors: Nicolas Plumere, Bochum (DE); Wilbur H. Campbell, Lake Linden, MI (US); Ellen R. Campbell, Lake Linden, MI (US)

(73) Assignee: The Nitrate Elimination Co., Inc., Lake Linden, MI (US)

( * ) Notice: Subject to any disclaimer, the term of this patent is extended or adjusted under 35 U.S.C. 154(b) by 748 days.

(21) Appl. No.: 13/400,974

(22) Filed: Feb. 21, 2012

(65) Prior Publication Data

US 2012/0211372 A1 Aug. 23, 2012

Related U.S. Application Data

(60) Provisional application No. 61/445,168, filed on Feb. 22, 2011.

(51) Int. Cl.
*C12Q 1/26* (2006.01)
*C12Q 1/30* (2006.01)
*G01N 33/53* (2006.01)

(52) U.S. Cl.
CPC .. *C12Q 1/26* (2013.01); *C12Q 1/30* (2013.01); *G01N 33/5308* (2013.01)

(58) Field of Classification Search
CPC ............ C12Q 1/005; C12Q 1/36; C12Q 1/30; C12Q 1/26; G01N 33/5308; G01N 27/372
USPC ........ 205/775, 777.5, 780, 780.5, 787.5, 792; 204/403.01–403.15
See application file for complete search history.

(56) References Cited

U.S. PATENT DOCUMENTS

| 2,482,724 | A | | 9/1949 | Baker | |
|---|---|---|---|---|---|
| 4,018,651 | A | * | 4/1977 | Canto et al. | ..................... 435/14 |
| 4,340,448 | A | | 7/1982 | Schiller et al. | |
| 5,776,715 | A | | 7/1998 | Garnham | |
| 7,160,690 | B2 | | 1/2007 | Orser et al. | |
| 2005/0221029 | A1 | | 10/2005 | Cater et al. | |
| 2010/0297737 | A1 | * | 11/2010 | Barkeloo et al. | ......... 435/252.34 |

FOREIGN PATENT DOCUMENTS

| AU | | 637585 | | 5/1990 |
|---|---|---|---|---|
| DE | | 150656 | A * | 9/1981 |
| JP | | 56142448 | A * | 11/1981 |

OTHER PUBLICATIONS

Gilvanda Silva Nunes and Jean-Louis Marty, Chapter 21: Immobilization of Enzymes on Electrodes, Methods in Biotechnology: Immobilization of Enzymes and Cell, Second Edition (2006).*

(Continued)

*Primary Examiner* — J. Christopher Ball
*Assistant Examiner* — Maris R Kessel
(74) *Attorney, Agent, or Firm* — Fish & Tsang LLP

(57) ABSTRACT

Systems and methods for oxygen removal from aqueous solutions are presented in which a bi-enzymatic reaction sequence recycles and depletes oxygen to extinction, preferably using an oxidase and a catalase as biocatalysts and a carbohydrate as co-substrate. Contemplated systems and methods are particularly advantageous in conjunction with electrochemical reaction systems in which oxygen would adversely interfere with the reaction system.

14 Claims, 8 Drawing Sheets

(56) References Cited

OTHER PUBLICATIONS

Faye H. Thorndycroft et al., A new assay for nitric oxide reductase reveals two conserved glutamate residues form the entrance to a proton-conducting channel in the bacterial enzyme, Biochem J., 1:401(1), pp. 111-119 (2007).*

Amine, A. et al, "Phosphate, Nitrate, and Sulfate Biosensors", Analytical Letters, vol. 37, No. 1, pp. 1-19, 2004.

Back, E. et al, "Isolation of cDNA clones coding for spinach nitrite reductase: complete sequence and nitrate induction", Molecular and General Genetics, vol. 212, No. 1, pp. 20-26, Apr. 1988.

Bellissimo, D.B. et al, "Expression of Spinach Nitrite Reductase in *Escherichia coli*: Site-Directed Mutagenesis of Predicted Active Site Amino Acids", Archive of Biochemistry and Biophysics, vol. 323, No. 1, pp. 155-163, Oct. 20, 1995.

Cui, Y. et al, "Development of a bienzyme system for the electrochemical determination of nitrate in ambient air", Analytical and Bioanalytical Chemistry, vol. 386, pp. 1567-1570, 2006.

Giblin, T. et al, "Perchlorate and nitrate reductase activity in the perchlorate-respiring bacterium perclace", Microbiological Research, vol. 156, pp. 311-315, 2001.

Glazier, S.A., "Contruction and Characterization of Bitrate Reductase-Based Amperometric Electrode and Nitrate Assay of Fertilizers and Drinking Water", Analytical Chemistry, vol. 70, pp. 1511-1515, 1998.

Israel, I. et al, "Expression of the iorAB genes from Brevundimonas diminuta 7 encoding the molybdenum hydroxylase isoquinoline 1-oxidoreductase in Pseudomonas putida", FEMS Microbiology Letters, vol. 210, pp. 123-127, 2002.

Israel, Y. et al, "Polarographic Study of Inhibitors and Catalysts for the Reaction of Dissolved Oxygen with Sulphite Ion", Talanta, vol. 14, pp. 925-931, 1967.

Larsen, L. H. et al, "Fast Responding Biosensor for On-Line Determination of Nitrate/Nitrite in Activated Sludge", Water Research, vol. 34, No. 9, pp. 2463-2468, 2000.

Mizuno, N. et al, "Crystal Structure of Dissimilatory Sulfite Reductase D (DsrD) Protein—Possible Interaction with B- and Z-DNA by Its Winged-Helix Motif", Structure, vol. 11, pp. 1133-1140, Sep. 2003.

Okeke, B.C. et al, "Molecular analysis of a perchlorate reductase from a perchlorate-respiring bacterium Perc1ace" Microbiological Research, vol. 158, pp. 337-344, 2003.

Plumere, N. et al, "Enzyme-Catalyzed O2 Removal System for Electrochemical Analysis under Ambient Air: Application in an Amperommetric Nitrate Biosensor", Analytical Chemistry, 2011.

Quan, D. et al, "A Nitrate Biosensor Based on Co-immobilization of Nitrite Reductase and Viologen-modified Chitosan on a Glassy Carbon Electrode", Sensor, vol. 10, pp. 6241-6256, 2010.

Quan, D. et al, "Electrochemical Determination of Nitrate with Nitrate Reductase-Immobilized Electrodes under Ambient Air", Analytical Chemistry, vol. 77, pp. 4467-4473, 2005.

Thorell, H.D. et al, "A Gene Cluster for Chlorate Metabolism in Ideonella dechloratans", Applied and Environmental Microbiology, vol. 69, No. 9, pp. 5585-5592, 2003.

Tripathy, J.N. et al, "The role of tryptophan in the ferredoxin-dependent nitrite reductase of spinach", Photosynthesis Research, vol. 94, pp. 1-12, 2007.

Wang, J., "Amperometric biosensors for clinical and therapeutic drug monitoring: a review", Journal of Pharmaceutical and Biomedical Analysis, vol. 19, pp. 47-53, 1999.

Wang, J., "Electrochemical Glucose Biosensors", Chemical Reviews, vol. 108, pp. 814-825, 2008.

Wilson, R. et al, "Glucose oxidase: an ideal enzyme" Biosensors & Bioelectronics, vol. 7, pp. 165-185, 1992.

Wolfe, M.T. et al, "Hydroxylamine Reductase Activity of the Hybrid Cluster Protein from *Escherichia coli*", Journal of Bacteriology, vol. 184, No. 21, pp. 5898-5902, 2002.

* cited by examiner

SYSTEMS AND METHODS FOR ENZYMATIC OXYGEN REMOVAL

This application claims priority to our U.S. provisional application with Ser. No. 61/445,168, which was filed Feb. 22, 2011.

FIELD OF THE INVENTION

The present application relates generally to oxygen ($O_2$) removal systems for use with biosensors that operate with recombinant reductases, and particularly with nitrate reductases, nitrite reductases, chlorate reductases, perchlorate reductases, hydroxylamine reductases, bisulfite reductases, and isoquinoline reductases.

BACKGROUND OF THE INVENTION

Many electrochemical biosensors for point of use applications have been developed over the last 30 years, and a common goal for such sensors is to achieve a fast response, preferably with single use device that makes possible the selective quantification of a target analyte in a complicated matrix without sample pre-treatment.

For example, amperommetric glucose biosensors are the most commercially successful products to result from this research and development effort. Besides such glucose biosensors, several other oxidase-based biosensors have been developed for medical and environmental applications. However, field application of biosensors based on reductases is often limited by the need for anaerobic conditions. For example, the reduction of nitrate catalyzed by nitrate reductase occurs at potentials more negative than the oxygen reduction reaction, and oxygen must therefore be removed from the sample before analysis. While nitrate biosensors for on-site determination of nitrate in water, soil or plant samples is potentially very valuable with respect to economic, environmental, and health issues, standard oxygen removal methods based on argon purging or vacuum degassing are not compatible with on-site monitoring. Such need for oxygen removal is not limited to nitrate reductases only, but is also generally required for numerous other reductase-based biosensors.

Recently the use of sodium sulfite as an oxygen scavenger for nitrate amperommetric biosensor based on recombinant eukaryotic nitrate reductase was described. However, the maximum sulfite concentration which does not affect the nitrate analysis is about 1 mM, which is often sufficient for large sample volumes or closed systems. However, in open systems (e.g., systems where the sample is exposed to atmospheric oxygen) or systems with sample volumes of 200 µL or less, it is typically not possible to maintain anaerobic conditions with sulfite for the time required for electrochemical measurements. Similar difficulties may be encountered in the system and methods described in U.S. Pat. No. 2,482,724 where an enzymatic system is used to reduce oxygen from food stuff in a closed container. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

The most recent advance in biosensor technology is the "electron-carrier free" system, where an enzyme is directly immobilized on the working electrode of the electrochemical cell (see e.g., U.S. Pat. No. 4,970,145). This may result in direct electron transfer from the electrode to the electron-carrying group of the enzyme, such that the enzyme is "wired" to the electrode. In this system, interference by oxygen is minimized unless the immobilized, reduced reductase reacts with oxygen. However, if the potential required to drive the detection reaction is more negative than the potential required for reducing oxygen (which may depend on the electrode material), then oxygen interference may occur. In these cases, an oxygen removal system will still be required to facilitate operation of the wired reductase biosensor.

Remarkably, the need for oxygen removal in solution extends well beyond the enzyme biosensors, and in fact, may be present in numerous alternative electrochemical systems. For example, various biofuel cells are operated under anaerobic conditions in some formulations (see e.g., US2010/0297737). In such case, an oxygen removal system will typically be required to facilitate operation of the biofuel cell.

Thus, even though various systems and methods are known to reduce oxygen in a liquid reaction system, all or almost all of them suffer from one or more disadvantage. Therefore, there is still a need to provide improved oxygen removal systems suitable for use with biosensors and other electrochemical reaction systems.

SUMMARY OF THE INVENTION

The inventors have now discovered that the above disadvantages can be readily overcome by use of an enzymatic oxygen reduction system that is particularly useful in combination with biosensors based on reductases. In especially preferred aspects of the inventive subject matter, reduction or elimination of oxygen is carried out in a bi-enzymatic system that employs oxygen and an aldohexose as substrates.

In one aspect of the inventive subject matter, a method of reducing oxygen from an aqueous medium of an electrochemical process includes a step in which an oxidase, an oxidase substrate, and a catalase are combined in an aqueous medium to so form a test medium for use in the electrochemical process. Most typically, the oxidase uses the oxidase substrate and dissolved oxygen in the test medium to produce a reaction product and hydrogen peroxide, and the oxidase and/or the oxidase substrate are selected such that the reaction product maintains (will not adversely affect) a parameter in the electrochemical process over a predetermined test period. The test medium is then incubated for a time sufficient to deplete the test medium of dissolved oxygen, and the electrochemical process is then performed within the predetermined test period.

In especially preferred aspect, test medium is a buffered aqueous medium, has a volume of equal or less than 1000 µL, and/or has a ratio of surface to volume of at least 1 $cm^{-1}$. It is further contemplated that the test medium is exposed to atmospheric oxygen. Most typically, the electrochemical process comprises a reductase reaction (e.g., nitrate reductase reaction) and/or amperometry and coulometry.

It is still further preferred that the oxidase is an aldohexose oxidase, an amine oxidase, an amino acid oxidase, an aldehyde oxidase, or a urate oxidase, and that the parameter in the electrochemical process is the pH of the test medium, the activity of an enzyme present in the electrochemical process, and/or reactivity of the reaction product. While not limiting to the inventive subject matter, it is generally preferred that the step of incubating the test medium is performed in equal or less than 10 minutes, and that the predetermined test period is equal or less than 4 hours, and more typically equal or less than 1 hour. In especially preferred aspects, the electrochemical process comprises reducing nitrate using a nitrate reductase and an electron transfer compound, and further comprises use of amperometry and/or coulometry. In such methods, the oxidase is a pyranose oxidase, and the oxidase substrate is glucose.

Therefore, the inventors also contemplate a kit that includes an oxidase, an oxidase substrate, and a catalase in quantities sufficient to allow formation of a test medium for use in an electrochemical process. Most preferably, the oxidase is capable to produce from the oxidase substrate and dissolved oxygen in the test medium a reaction product and hydrogen peroxide, wherein the oxidase and/or the oxidase substrate is selected such that the reaction product maintains a parameter in the electrochemical process over a predetermined test period. Contemplated kits will further include an enzyme for electrochemical detection or quantification of an analyte in the test medium.

Especially preferred kits will further include a buffer, an electron transfer compound, and/or an electrode. It is still further preferred that the oxidase is a pyranose oxidase and the oxidase substrate is glucose, and/or that the enzyme is a nitrate reductase.

Various objects, features, aspects and advantages of the present invention will become more apparent from the following detailed description of preferred embodiments of the invention.

DETAILED DESCRIPTION

The inventors have discovered that oxygen can be removed from an aqueous medium in a conceptually simple and effective manner that depletes the medium from oxygen using substrates that exhibit little to no interference with reactions needed to electrochemically quantify one or more analytes. Systems and methods presented herein are especially advantageous where the electrochemical detection/quantification is based on an enzymatic oxygen reduction system that is particularly useful in combination with biosensors based on reductases.

In especially preferred aspects of the inventive subject matter, reduction or elimination of oxygen is carried out in a bi-enzymatic system that uses oxygen and an aldohexose as substrates to generate an oxidized carbohydrate and hydrogen peroxide, which is then converted to water and oxygen in a disproportionation reaction catalyzed by a catalase. So produced oxygen is then eliminated by the aldohexose. Remarkably, as the catalase catalyzes the disproportionation of hydrogen peroxide at significantly faster rates that the aldohexose reductase produces hydrogen peroxide, adverse effects of the hydrogen peroxide on the remaining test system are negligible. Moreover, as the oxygen produced by the catalase is recycled into the bi-enzymatic process, the solution can substantially be driven to oxygen exhaustion.

Figure 1:
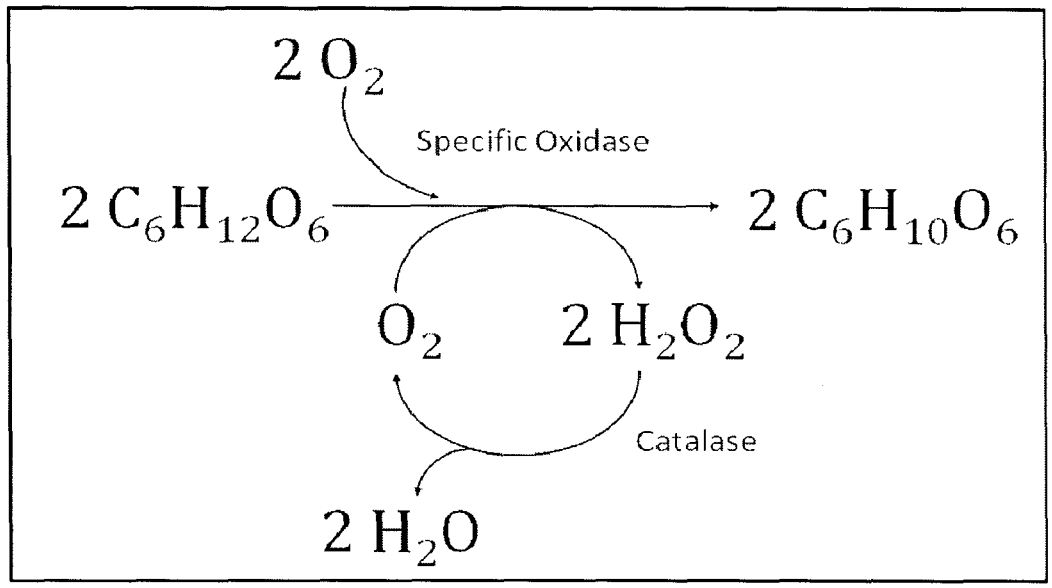
FIG. 1 is an exemplary reaction scheme illustrating various aspects of contemplated enzymatic oxygen removal systems according to the inventive subject matter.
Figure 2:
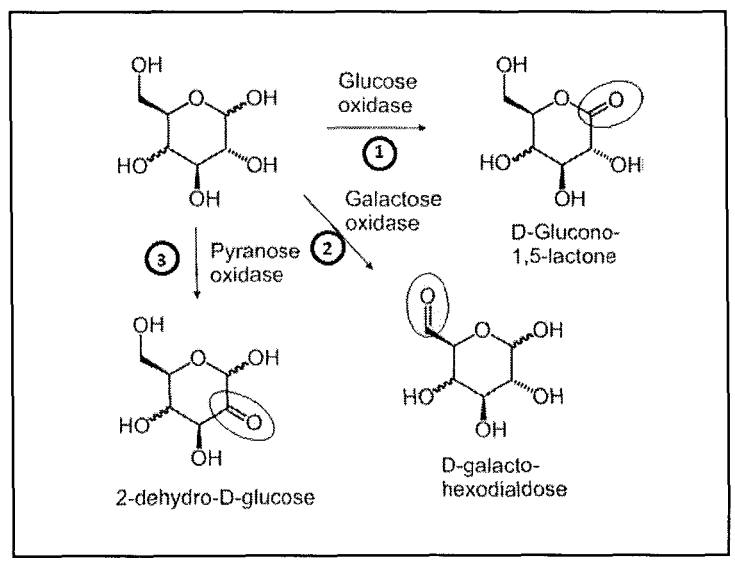
FIG. 2 illustrates various enzymatic reactions and reaction products of contemplated enzymatic oxygen removal systems according to the inventive subject matter.

An exemplary schematic overview over a set of bi-enzymatic reactions is illustrated in FIG. 1. Here, two moles of an aldohexose substrate are converted by an aldohexose specific oxidase enzyme to two moles of the corresponding reaction products with concurrent formation of two moles of hydrogen peroxide. A catalase then converts the two moles of hydrogen peroxide to two moles of water and one mol of molecular oxygen, which re-enters the reaction sequence to extinction. Thus, the oxygen in the solution arising from either the reaction sequence or diffusion from the gaseous environment is essentially entirely removed and the solution is maintained in an anaerobic condition. FIG. 2 schematically illustrates exemplary embodiments for the first enzymatic reaction where an aldohexose substrate is converted by an aldohexose specific oxidase enzyme to the corresponding lactone (e.g., via glucose oxidase in reaction 1), a corresponding sugar aldehyde (e.g., via galactose oxidase in reaction 2), or a corresponding keto-sugar (e.g., via pyranose oxidase in reaction 3). Only partial reactions are shown omitting oxygen and hydrogen peroxide production.

As shown in more detail in the Equations I-III below, the reaction of an aldohexose with oxygen is catalyzed by the corresponding oxidase (Equation 1). In a second step, the hydrogen peroxide resulting from this reaction is disproportionated into water and molecular oxygen by a catalase (Equation 2), and the so generated oxygen are further reduced by the aldohexose. In the net reaction, it should therefore be appreciated that two aldohexose molecules are necessary for the reduction of one oxygen molecule (Equation 3), and that the only net reaction products in this sequence besides the oxidized aldohexose is water.

Oxidase Reaction: $2O_2 + 2C_6H_{12}O_6 \rightarrow 2C_6H_{10}O_6 + 2H_2O_2$   Eq. 1

Catalase Reaction: $2H_2O_2 \rightarrow O_2 + 2H_2O$   Eq. 2

Net Reaction: $O_2 + 2C_6H_{12}O_6 \rightarrow 2C_6H_{10}O_6 + 2H_2O$   Eq. 3

Viewed from another perspective, it should be recognized that the use of relatively inert aldohexoses as reducing agents for oxygen opens the possibility to introduce high concentration of the aldohexoses for achieving oxygen depletion in small volumes for extended time periods under ambient air without affecting the bio-recognition component of the reductase biosensor. Thus, depending on the nature of the biosensor or electrochemical reaction with respect to the reactivity of the oxidation products ($C_6H_{10}O_6$) from the particular aldohexose will determine which enzyme will be the preferred choice. In this context, it should be appreciated that the three different oxidase enzymes shown in FIG. 2 (glucose oxidase, galactose oxidase, and pyranose oxidase) each catalyze the oxidation of a different hydroxyl group of the aldohexose. For example, glucose oxidase catalyzes the oxidation of the hemi-acetal of glucose to the corresponding lactone, which in water tends to hydrolyze to glucuronic acid, thus acidifying the reaction mixture as oxygen is removed. On the other hand, galactose oxidase catalyzes the reaction of the primary alcohol in galactose to the corresponding aldehyde, which is a reactive molecule with the capacity to inactivate some enzymes by reactions with amine-containing amino acid side chains in the polypeptide backbone of the enzyme. In yet another example, pyranose oxidase catalyzes the oxidation of a secondary alcohol of glucose to the respective ketone, which is a relatively non-reactive product. Thus, depending on the reductase enzyme utilized in the biosensor, a compatible choice for the oxygen removal system can be formulated.

Figure 3:
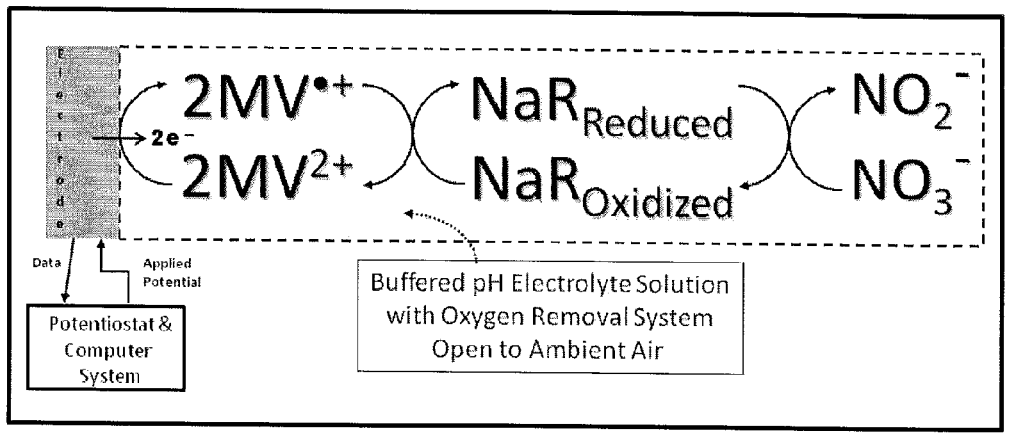
FIG. 3 is a schematic for operation of an exemplary reductase biosensor employing methyl viologen as the electron-carrying dye, a recombinant nitrate reductase as the enzyme, and nitrate as the analyte.

According to the present invention, "off-the-shelf" screen-printed electrochemical cells (SPE) with carbon or metallic electrodes and silver pseudo-reference or other reference electrodes and a small volume reaction well are widely available today from a number of commercial manufacturers. These devices are suitable for formulating reductase biosensors without undue experimentation for detection and monitoring of a variety of inorganic and some organic analytes. One exemplary scheme for formulating a reductase biosensor is illustrated in FIG. 3. Here, methyl viologen is used as an electron-carrying dye, a recombinant nitrate reductase is employed as the enzyme, and nitrate is the analyte. In the example of FIG. 3, the enzyme, dye, and analyte are contained in a pH buffered electrolyte solution, which also contains the bi-enzymatic oxygen removal system. A conventional potentiostat supplies and applies a potential and also collects the data for current consumed and charge utilized during the specific time the potential is applied.

The operation of an exemplary reductase biosensor can be generally characterized as follows: An aqueous electrolyte solution that includes a suitable buffer, an electron-carrying dye, a water-soluble recombinant reductase enzyme, an aldohexose, an aldohexose oxidase enzyme, and catalase is transferred to the reaction well of an SPE and allowed to stand for a limited time of approximately 1 minute. This allows the enzyme to equilibrate with the solution components, the oxygen removal system to reduce endogenous oxygen essentially rendering the solution anaerobic, and for the system to reach an even distribution of the components in the electrolyte solution at the ambient temperature, which is typically from 10 to 50° C. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary. After this rest period, a potentiostat is used to supply direct electric current to the working electrode of the reductase biosensor, which is poised at a sufficiently negative potential using the reference electrode of the SPE to reduce an electron-carrying dye in the electrolyte solution contained in the reaction well of the SPE. The reduced dye directly reduces the reductase enzyme in the electrolyte solution which contains an electro-active chemical group bound to the polypeptide backbone of the enzyme, and the oxidized dye is returned to electrode to be recycled. The reduced reductase catalyzes the reduction of the target analyte present in the electrolyte solution in the SPE reaction well and the oxidized reductase becomes available for another reduction cycle.

The electric current and accumulated charge generated by the reductase-catalyzed reaction in the well of the SPE are recorded via the potentiostat for a pre-determined time period and stored in the computer system operating the potentiostat. The computer program compares the recorded electric current and accumulated charge to standard curves for the target analyte, which were analyzed at the same ambient temperature as the unknown analyte, to determine the concentration of the target analyte in the original sample. The standard curves for response of the electric current and accumulated charge are previously prepared by analysis of standard solutions of the target analyte under identical conditions used for analysis of unknown concentrations of target analyte and stored in the computer system. In complex sample matrices, a background current may be present in the absence of the recombinant reductase enzyme and this background must be subtracted from the current generated by the target analyte in the complete system to obtain the net current. Most typically, such correction can be achieved by use of accumulated charge as a normalizing factor. The pH of the electrolyte solution and the electron-carrying dye are matched to the recombinant reductase enzyme used to formulate the reductase biosensor. The oxygen removal system is also matched to the recombinant reductase enzyme to avoid interference with the recombinant reductase enzyme's functionality due to reaction with the oxidized aldohexose product accumulating from oxygen reduction as discussed above.

Electrodes are not limiting to the inventive subject matter so long as the electrode system is suitable for use in an electrochemical detection and/or quantification system. Therefore, all known and commercially available electrode materials and systems are deemed suitable for use herein. Among other things, contemplated electrodes include various screen printed electrodes, noble metal electrodes, and carbon electrodes (e.g., pyrolytic graphite electrodes). While it is contemplated that the systems and methods presented herein are deemed suitable for use with any volume of electrolyte or test medium, it is generally preferred that the volume of the test medium is relatively small, and typically less than 10 ml, more typically less than 5 ml, even more typically equal or less than 1 ml, and most typically equal or less than 0.2 ml.

In such relatively small test volumes, it should be noted that the surface area to volume ratio may present a significant factor for oxygen absorption via the gas/liquid interface, and that otherwise suitable systems may no longer be capable to accommodate such absorption. Thus, and viewed from a different perspective, contemplated systems and methods are particularly suitable for situations where the test medium has a ratio of surface to volume of at least $0.5\ cm^{-1}$, more typically at least $1\ cm^{-1}$, and most typically at least $2\ cm^{-1}$.

Similarly, it should be appreciated that the oxygen removal system presented herein is not limited to use in conjunction with a specific oxidase, but that all known oxidases are deemed suitable or use herein. Thus, all enzymes under the EC 1.x.x.x classification are appropriate. Viewed form another perspective, suitable oxidases include those that contain one or more redox active groups bound to an apo-protein of the enzyme, and/or those that can be reduced by a reduced dye as a substitute for the natural electron donor. Therefore, and among other suitable oxidases, especially preferred oxidases include aldohexose oxidases, amine oxidases, amino acid oxidases, aldehyde oxidase, and urate oxidases.

Similarly, the nature of the electrochemical reaction need not be limited to a nitrate reductase, and it should be appreciated that numerous alternative enzymes are also deemed suitable for use herein. For example, contemplated reductases include various nitrate reductases, and especially recombinant eukaryotic nitrate reductases (e.g., AtNaR2, EC 1.7.1.1; and YNaR1, EC 1.7.1.3 from The Nitrate Elimination Co., Inc., Lake Linden, Mich. 49945 USA), recombinant plant nitrite reductase (NiR, EC 1.7.7.1) that has been described elsewhere and expressed in *Escherichia coli*, chlorate reductase (ClR; EC 1.97.1.1) that has been described elsewhere and cloned from *Ideonella dechloratans*, perchlorate reductase (PClR; EC 1.97.1.1) described elsewhere, hydroxylamine reductase (HNH3R; EC 1.7.99.1) described elsewhere, bisulfite reductase (BiS; EC 1.8.99.3) described elsewhere, and isoquinoline reductase (IqR; EC 1.3.99.16) described elsewhere.

Depending on the type of reductase enzyme used, the person of ordinary skill in the art will readily be able to chose the appropriate buffer system to so achieve a functional enzymatic system as well as ensure proper electrode function. Alternatively, and depending on the nature of the electrode and enzyme used, direct oxidation/reduction of the enzyme by the electrode is also deemed suitable for use herein. Moreover, it should be appreciated that the oxygen removal system according to the inventive subject matter is not limited to application with a reductase biosensor, but may be applied to any electrochemical system in which removal of oxygen in an aqueous phase is desirable. For example, suitable electrochemical systems include reactors for electrochemical synthesis, fuel cells, etc. Still further, it should be noted that the oxygen removal system according to the inventive subject matter is also suitable for use in chemical reaction systems in which exclusion of oxygen is desirable.

While not limiting to the inventive subject matter, it is also contemplated that the aqueous system may be circulated through a molecular sieve bed or size exclusion membrane (or other separation system) to remove the oxidation product in a continuous or intermittent fashion. The enzymes may be retained in the solution or also be removed as appropriate.

EXAMPLES

A. Oxygen Removal Systems for the Reductase Biosensor

The aldohexose-oxidase-catalase system was tested with respect to its ability to remove oxygen and maintain an anaerobic condition in an open electrochemical cell under ambient air. Two types of electrochemical cells were used: A standard cell with 2.0 mL of electrolyte solution and about 0.8 $cm^2$ of ambient air/electrolyte interface. Ag/AgCl reference electrode, platinum counter electrodes and pyrolytic graphite working electrodes (PGE) were used. For low volume measurements, single-use screen printed electrodes (SPE) with 300 μL wells were used. The working and counter electrode material is carbon and the pseudo-reference electrode material is silver. The electrolyte volume was either 100 or 200 μL. The surface area of the interface with air was ~0.2 $cm^2$. The SPE based electrochemical cell is used as the model for field applications. The presence of oxygen was monitored with cyclic voltammetry. When oxygen is present in the electrolyte the reduction signal appears at potentials lower than −50 mV vs Normal Hydrogen Electrode at pH 7. The test solution was exposed to atmospheric oxygen throughout the entire measurement.

Figure 4:
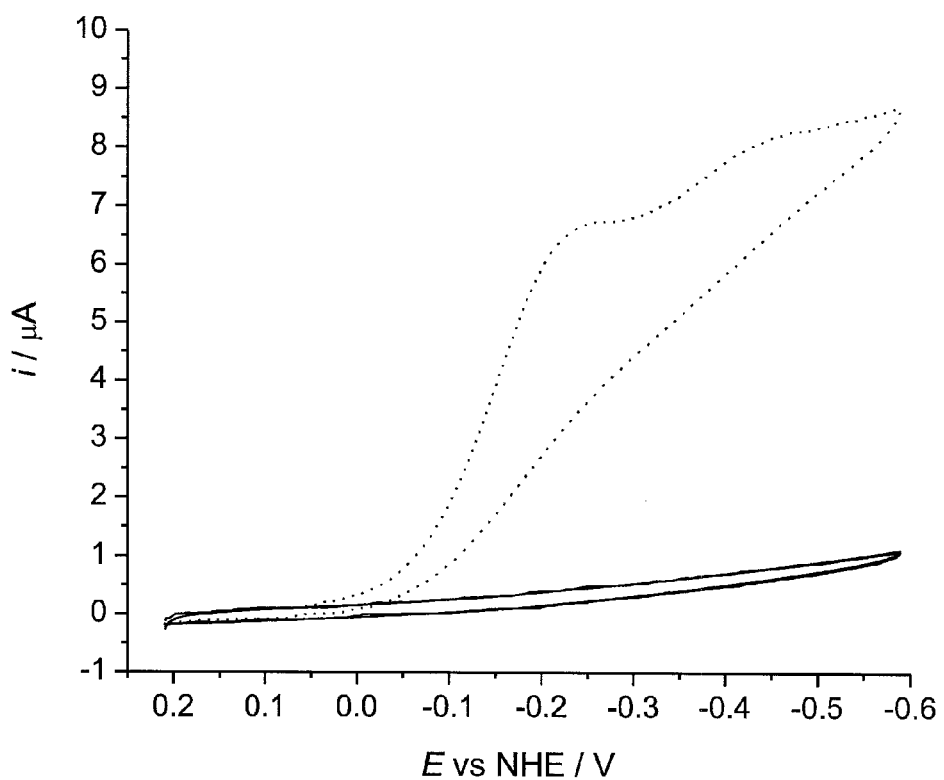
FIG. 4 presents an exemplary cyclic voltammogram of oxygen reduction measured with pyrolytic graphite working electrodes (PGE).

As can be readily seen from FIG. 4, the aldohexose/oxidase/catalase system efficiently removes oxygen from the solution. Here, the cyclic voltammogram was measured at a scan rate of 2 mV/s in 2.0 mL of 50 mM sodium 3-(N-morpholino) propanesulfoninate (MOPS), pH 7.0, with 20 μM sodium ethylenediamine tetraacetate (EDTA), and 20 mM glucose (upper scan with dotted line), and cyclic voltammograms after addition of glucose oxidase at 7 mg/mL and catalase at 4 mg/mL (lower scan lines, 3 scans). NHE=Normal hydrogen electrode. No waiting time is necessary to obtain a cyclic voltammogram (CV) without an $O_2$ signal. When the oxidase and catalase concentrations are as low as 1 mg/mL, no oxygen signal is detected. With 20 mM glucose the solution was oxygen-free for at least 2 hours in the 2 mL electrochemical cell. The results were identical whether glucose oxidase, pyranose oxidase, or galactose oxidase was used with their respective substrate in presence of catalase. In the case of the SPE well with 100 μL of electrolyte, oxygen is detected in the solution after 1 hour under ambient air, indicating that the aldohexose has been fully consumed. Although 1 hour is sufficient for electrochemical measurements in most biosensor applications, higher aldohexose concentrations were tested as well. This is of particular importance in the cases where very low sample volumes are desired. With 50 mM aldohexose in the SPE wells with 100 μL of electrolyte, anaerobic conditions were maintained for at least 1 h.

These experiments demonstrate that the aldohexose/oxidase/catalase system makes it possible to maintain anaerobic conditions in low volume electrochemical cells under ambient air conditions. Moreover, it should be noted that the various reagents, catalysts, and reaction products involved in the oxygen reduction reaction are not redox-active in the electrochemical window of interest for a reductase biosensor. While the electrochemical reduction of the $H_2O_2$ produced from the oxygen reduction may theoretically occur at the electrode surface, it should be recognized that sufficient quantities of catalase ensures that the hydrogen peroxide concentration remains low enough to avoid any electrochemical detection of this reaction intermediate. Thus, absence of electrochemical interference due to the oxygen removal system was demonstrated.

To test the oxygen removal system for possible interference with the bio-recognition element (e.g., a nitrate reductase), a eukaryotic nitrate reductase was used as the model for the bio-recognition element for the detection of nitrate in water. In the reductase biosensor for nitrate, nitrate reductase (NaR) is typically used with the electron-carrying dye methyl viologen (MV) in solution as the electron mediator. In this case, reduction of nitrate takes place at potentials more negative than −300 mV vs Normal Hydrogen Electrode at pH 7 and is therefore subject to oxygen interference. The reductase biosensor for nitrate using NaR and MV in solution was tested in presence of the enzyme-based oxygen removal system. The NaR activity in presence of a constant, saturating nitrate concentration was monitored with cyclic voltammetry. The catalytic current due to the nitrate reduction was used as a measure of the NaR activity.

Figure 5A:
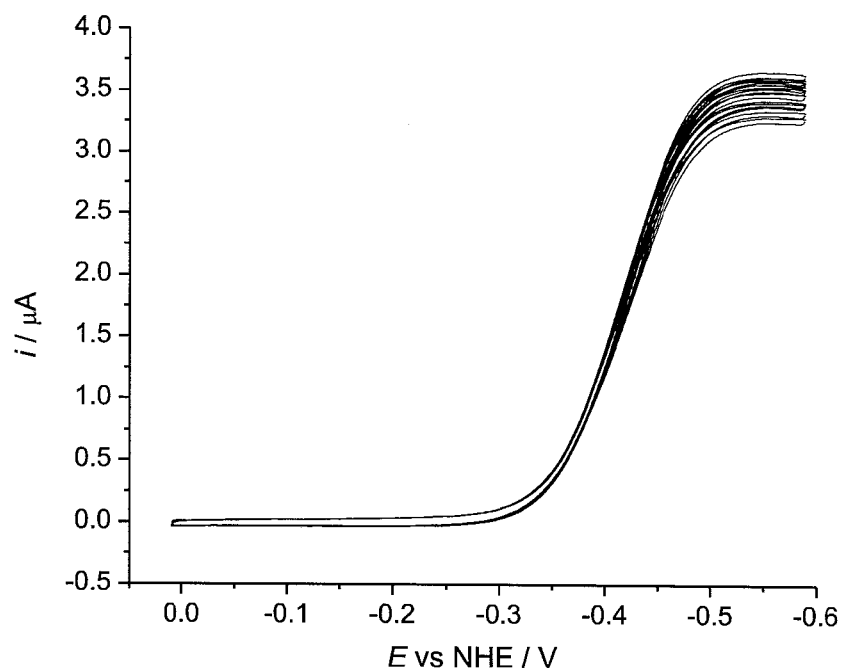
FIG. 5A depicts exemplary cyclic voltammograms measured at intervals over 4 hours with PGE.
Figure 5B:
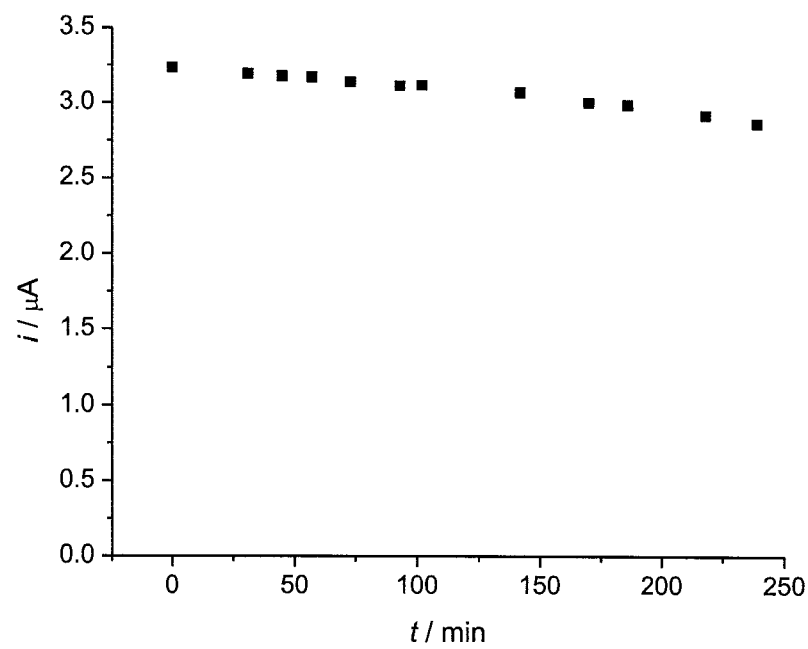
FIG. 5B is a graph depicting the decrease in maximum catalytic current observed in the cyclic voltammograms of FIG. 5A over time.
Figure 6A:
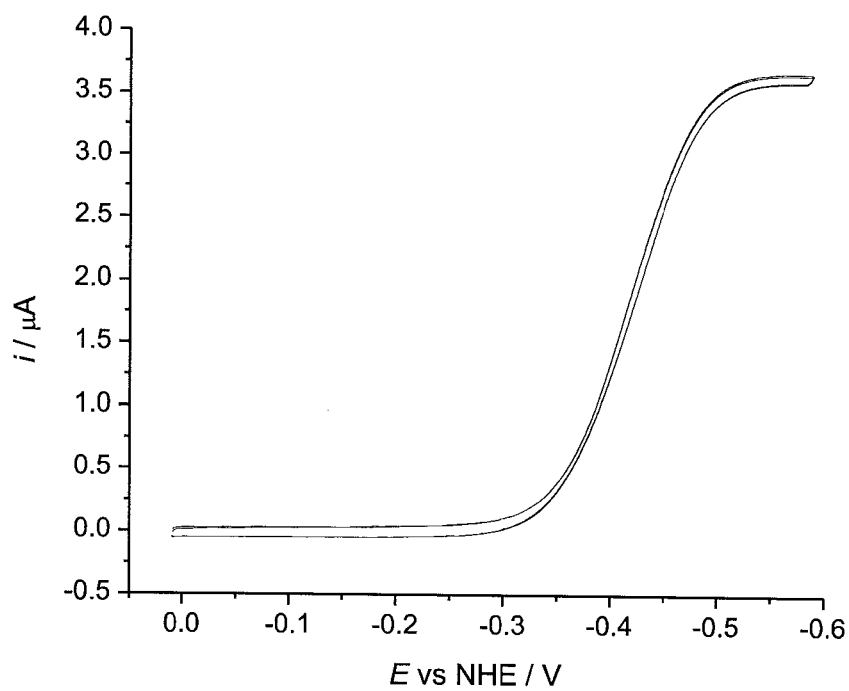
FIG. 6A depicts exemplary cyclic voltammogram measured at intervals over 2.5 hours with PGE.
Figure 6B:
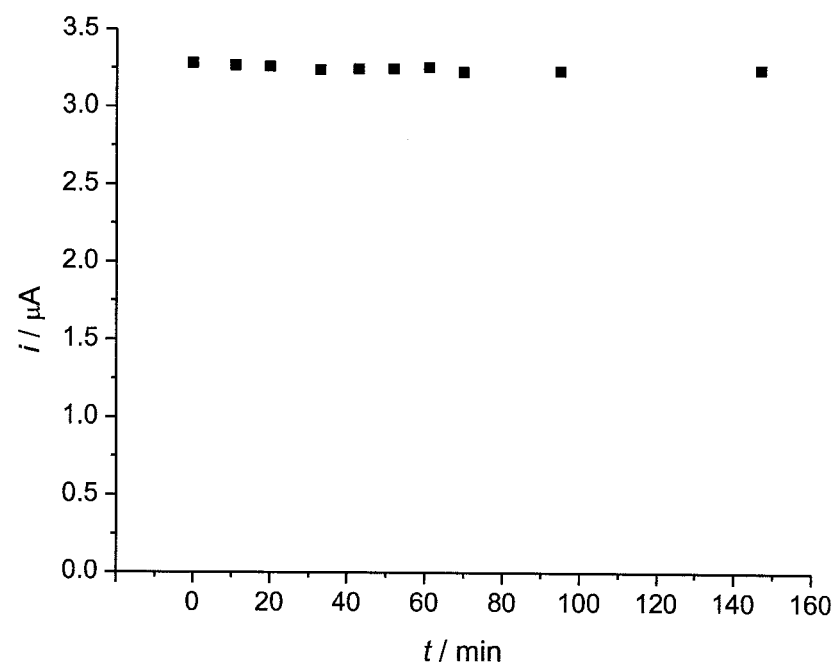
FIG. 6B is a graph depicting the decrease in maximum catalytic current observed in the cyclic voltammograms of FIG. 6A over time.

In the case of glucose oxidase used in contemplated oxygen removal system, the cyclic voltammogram displayed the S-shape typical for a catalyzed redox process where nitrate reduction to nitrite is catalyzed by the NaR in presence of MV. FIG. 5A depicts typical exemplary cyclic voltammograms for such reaction measured at intervals over 4 hours with PGE at a scan rate of 2 mV/s in 2.5 mL of 50 mM MOPS, pH 7.0, with 50 µM MV, 2.5 mM $KNO_3$, 20 µM EDTA, 50 mM glucose, glucose oxidase at 1 mg/mL, catalase at 0.5 mg/mL, and 3 units of YNaR1. NHE=Normal hydrogen electrode. The activity of the enzyme is comparable to the one obtained when the anaerobic conditions are achieved by argon purging. Therefore, the initial activity of NaR is not affected by the enzymatic oxygen removal system. On the other hand, the loss of activity over 4 hours is 11.3% as is illustrated in FIG. 5B showing is a graph that evidences the decrease in maximum catalytic current observed in the cyclic voltammograms of FIG. 5A over time. This demonstrates that a product resulting from the reaction between glucose and oxygen inhibited the NaR activity and the detection of nitrate in the system to at least some extent. From the two products of this reaction, water and D-(+)-gluconic acid δ-lactone, the latter, which hydrolyzes to glucuronic acid in water, may be responsible for this inhibition. The pH of the reaction mixture was taken after the 4 hour series of CV scans and found to be 5.96, which indicates the generation of acid during oxygen removal overcame the capacity of the buffer in the system. The reaction intermediate, hydrogen peroxide, is not likely to participate in the NaR inhibition. Indeed, the absence of redox signal for $H_2O_2$ demonstrates that it is quickly disproportionated by catalase in this system. Remarkably, when the same experiment was repeated with the SPE in the low volume open wells containing 100 µL of reaction solution, a even faster decrease in activity was observed. The faster inhibition occurring in the lower electrolyte volumes of the SPE wells in comparison to the PGE cell suggested that a product resulting from the reaction between glucose and oxygen, inhibited NaR activity. From the two products of this reaction, water and D-(+)-gluconic acid δ-lactone, the latter may be responsible for this inhibition. Indeed, the lactone is quickly hydrolyzed to gluconic acid, which lowers the pH of the solution and therefore, affects the nitrate reductase activity. A simple way to overcome this problem is to increase the concentration of the buffer in the system, which will increase its capacity to take up acid during the course of the experiment. As shown in FIGS. 6A and 6B, when 200 mM sodium 3-(N-morpholino) propanesulfoninate (MOPS), pH 7.0, pH 7.0, is used in the reaction mixture, the NaR activity is stable for up to 2.5 hours. More specifically, FIG. 6A shows exemplary cyclic voltammograms measured at intervals over 2.5 hours with PGE at a scan rate of 2 mV/s in 2.0 mL of 200 mM MOPS, pH 7.0, with 50 µM MV, 2.5 mM $KNO_3$, 20 µM EDTA, 50 mM glucose, Glucose oxidase at 1 mg/mL, catalase at 0.5 mg/mL, and 3 units of YNaR1. NHE=Normal hydrogen electrode, and FIG. 6B is a graph depicting the decrease in maximum catalytic current observed in the cyclic voltammograms of FIG. 6A over time.

In summary, the use of higher buffer concentration makes it possible to circumvent the loss of NaR activity due to the decrease in pH resulting from the hydrolysis of gluconolactone to gluconic acid. However at high buffer concentration (500 mM) the maximum NaR activity is significantly lower, which is the main drawback of this strategy. Therefore increasing buffer concentration may not be adapted for all reductase biosensors. Still, the use of 200 mM MOPS as the buffer is adequate for nitrate reductase in the glucose oxidase/catalase system with respect to both maximum catalytic activity and stability. Therefore, this system can be used to maintain anaerobic conditions in an open electrochemical cell as long as acid production does not exceed the buffer capacity of the system or all of the glucose is consumed. The time over which anaerobic conditions are maintained will depend on the electrolyte volume, gas liquid interface surface area and diffusion kinetics of oxygen into the electrolyte. As an example, in the 2 mL cell with 200 mM MOPS, pH 7.0, the loss in NaR activity observed after 2.5 hours is only 1%.

Figure 7A:
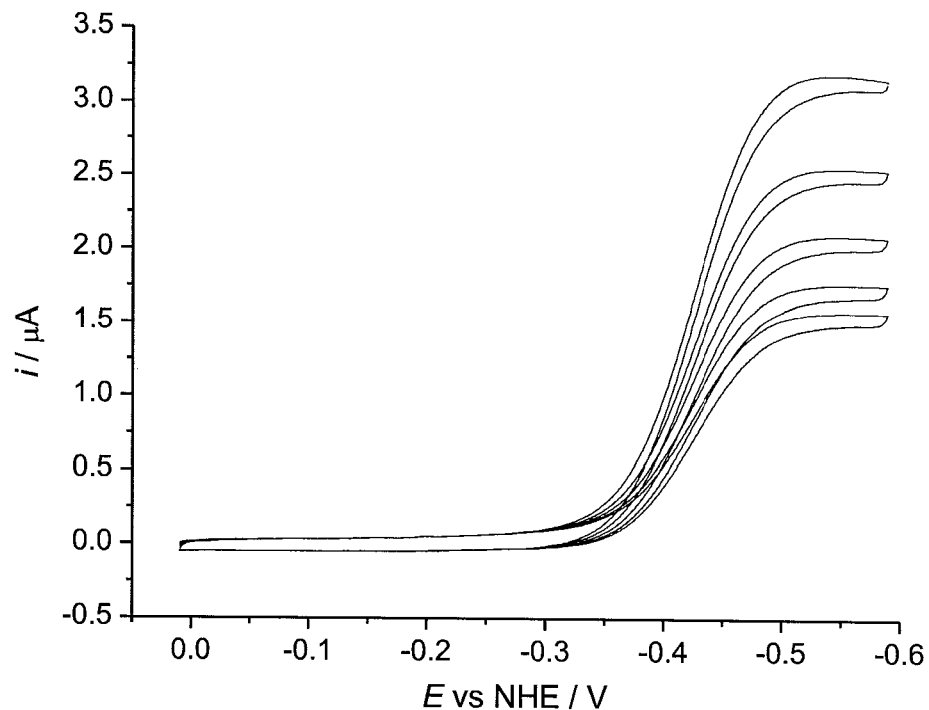
FIG. 7A depicts exemplary cyclic voltammograms measured at intervals over 50 minutes with PGE.
Figure 7B:
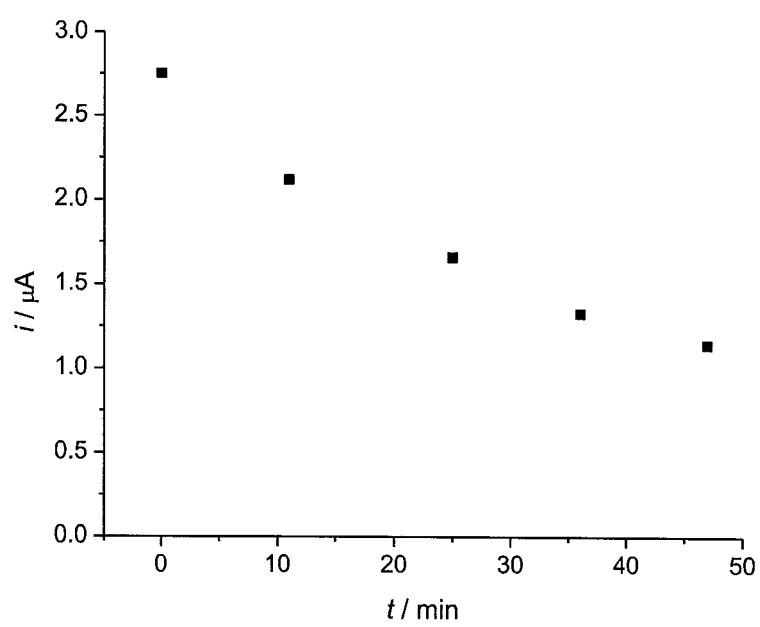
FIG. 7B is a graph depicting the decrease in maximum catalytic current observed in the cyclic voltammograms of FIG. 7A over time.

Instead of increasing the buffer concentration to limit the effect of gluconic acid production on the nitrate reductase activity, an alternative oxidase, that involves the production of a pH-neutral product, was used. The oxidation of galactose with galactose oxidase, involves the oxidation of a primary alcohol to an aldehyde. The product, D-galacto-hexodialdose, is expected not to affect the pH of the solution. Still, the activity of the nitrate reductase decreased relatively fast when galactose oxidase in presence of galactose and catalase are used for the oxygen removal system. Although the pH value of the electrolyte is stable at 7.0, the loss of NaR activity over 47 min is 58.6%. More particularly, FIG. 7A depicts cyclic voltammograms measured at intervals over 50 minutes with PGE at a scan rate of 2 mV/s in 2.5 mL of 50 mM MOPS, pH 7.0, with 50 µM MV, 2.5 mM $KNO_3$, 20 µM EDTA, 50 mM galactose, galactose oxidase at 1000 units/mL, catalase at 1 mg/mL, and 3 units of YNaR1. NHE=Normal hydrogen electrode, and FIG. 7B is a graph depicting the decrease in maximum catalytic current observed in the cyclic voltammograms of FIG. 7A over time. In this case, it is believed that the aldehyde group reacts with primary amine residues within the active site of nitrate reductase which results in the enzyme deactivation. Therefore, galactose oxidase-based oxygen removal system is less preferred to maintain anaerobic conditions for reductase biosensors for nitrate. It may only be applied for reductase biosensors based on reductase enzymes that are not affected by the aldehyde functionality.

Figure 8A:
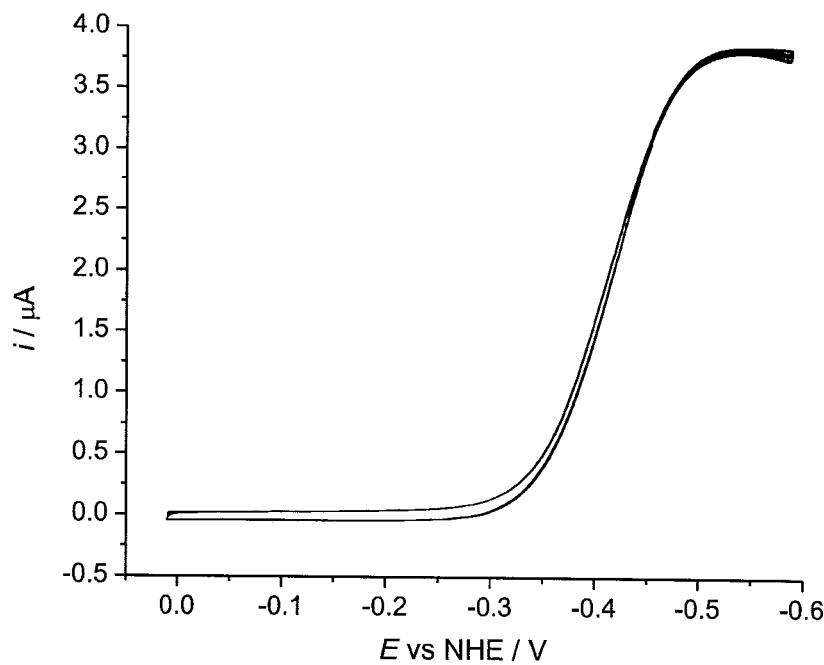
FIG. 8A depicts exemplary cyclic voltammograms measured at intervals over 250 minutes with PGE.
Figure 8B:
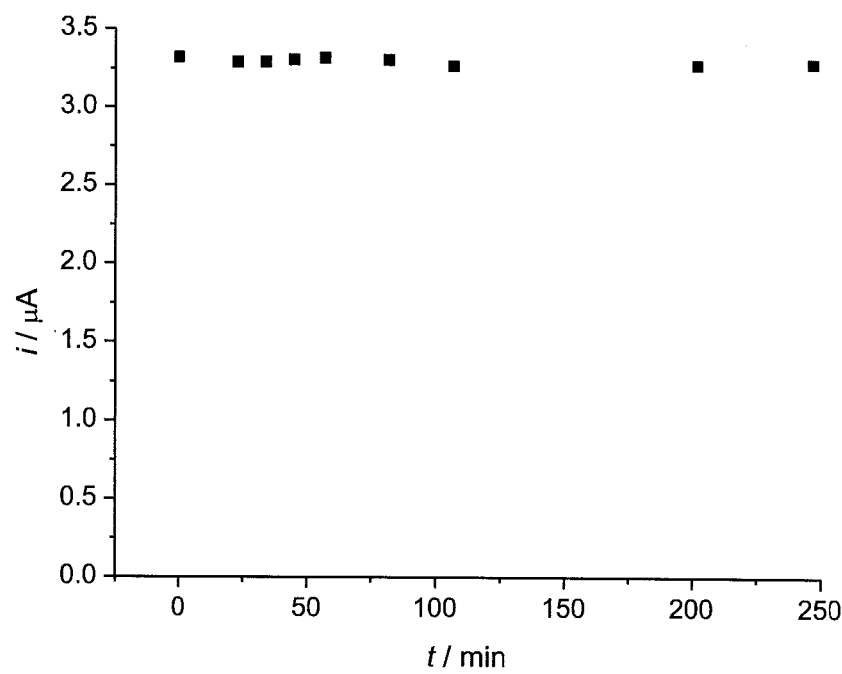
FIG. 8B is a graph depicting the decrease in maximum catalytic current observed in the cyclic voltammograms of FIG. 8A over time.

The last enzyme, pyranose oxidase was chosen to circumvent the drawback of both glucose oxidase and galactose oxidase. The oxidation of glucose with pyranose oxidase, involves the oxidation of secondary alcohol to a ketone, which is not expected to react with amine groups in the enzyme under the measurement conditions. The pH of the solution should not be affected by this reaction as well. Remarkably, with the pyranose oxidase oxygen removal system, virtually no loss of NaR activity was observed, and enzyme activity decreased by only 0.9% over 4 hrs. FIG. 8A shows cyclic voltammograms measured at intervals over 250 minutes with PGE at a scan rate of 2 mV/s in 2.5 mL of 50 mM MOPS, pH 7.0, with 50 µM MV, 2.5 mM $KNO_3$, 20 µM EDTA, 50 mM glucose, pyranose oxidase at 0.5 mg/mL, catalase at 0.5 mg/mL, and 3 units of YNaR1. NHE=Normal hydrogen electrode, and FIG. 8B depicts the decrease in maximum catalytic current observed in the cyclic voltammograms of FIG. 8A over time. Since the pH is not impacted, there is no need to adjust buffering strength. Employing this oxygen removal system permits development of reductase biosensors with very small reaction volumes. This system can be used to maintain anaerobic conditions in an open electrochemical cell as long as all the glucose substrate is not consumed. Thus, since glucose concentration can be very high (for example, 1 molar glucose), anaerobicity can be maintained almost indefinitely.

In summary, pyranose oxidase or glucose oxidase (with increased MOPS concentration) do not affect the activity of nitrate reductase for extended times while maintaining anaerobic conditions in the open electrochemical cell. Therefore, these enzymes may be used for reductase biosensor applications based on nitrate reductase. This will be demonstrated for the glucose oxidase-glucose-catalase system in the following.

B. Model System for the Reductase Biosensor with Enzymatic Oxygen Removal System An exemplary reductase biosensor was modeled using commercially available screen printed electrode cells with 300 μL wells (SPE). The SPE are single use electrodes and are suitable systems for field analysis. Samples tested included plant leaf tissue extracts prepared in the laboratory in a manner similar to field analysis samples. The complicated plant extract matrix is a good test system for demonstrating the reductase biosensor for nitrate. The measurement procedure was based on measuring the electrochemical signal due to the reduction of the nitrate in the samples by nitrate reductase in solution with methyl viologen as the electron mediator, as shown in FIG. 3.

Figure 9:
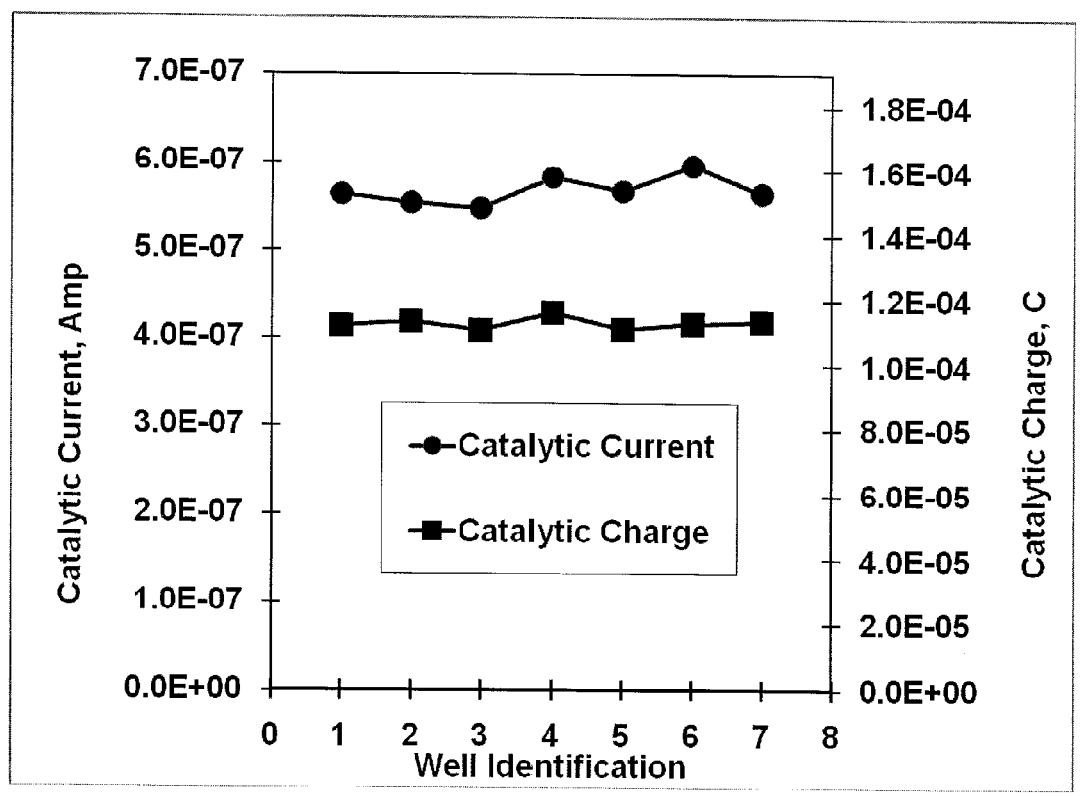
FIG. 9 is a graph illustrating the maximum catalytic current and charge for several chronocoulommetry measurements in different screen printed electrodes (SPE) wells at fixed redox potential.

In a first experiment, the reproducibility of the current signals from the SPE at constant nitrate concentration was tested for 200 μL of total volume and results are depicted in FIG. 9. Here, the graph depicts maximum catalytic current and charge for several chronocoulommetry measurements in different SPE wells at fixed redox potential of −1000 mV in 200 μL of 200 mM MOPS, pH 7.0, with 50 μM MV, 2.5 mM $KNO_3$, 20 μM EDTA, 50 mM glucose, glucose oxidase at 0.5 mg/mL, catalase at 0.5 mg/mL, and 1.2 units of YNaR1, after the potential is applied for 180 seconds. Ambient temperature=22° C. The relative standard deviation from the measurements of 8 different SPEs for the current and charge values are 2.95% and 1.86%, respectively. The key parameter for optimal reproducibility is to ensure that maximum NaR activity is achieved. For this purpose it is important that gentle mixing is used and a short waiting time (typically less than 5 minutes) after pipetting the solution into the SPE wells is utilized before the measurement. This allows the adjustment of NaR to the reaction solution. In comparison if mixing is performed with a pipette and in absence of waiting time, higher relative standard deviation for the current and charge values were obtained (3.2% and 2.6% respectively).

In a second experiment, the reductase biosensor for nitrate was modeled in SPE by calibrating the system with standard nitrate solutions. The experimental data were fitted to equation 4.

$$y = P1x/(P2+x) \quad \text{Eq. 4}$$

Figure 10A:
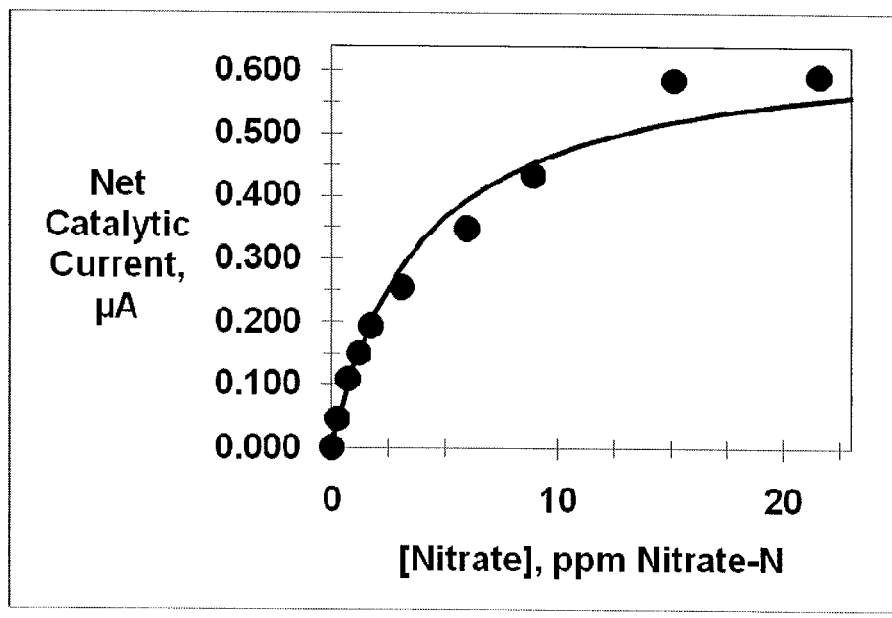
FIGS. 10A and 10B are graphs illustrating the increase in catalytic current and charge, respectively, with increasing $[NO_3^-]$ in SPE.
Figure 10B:
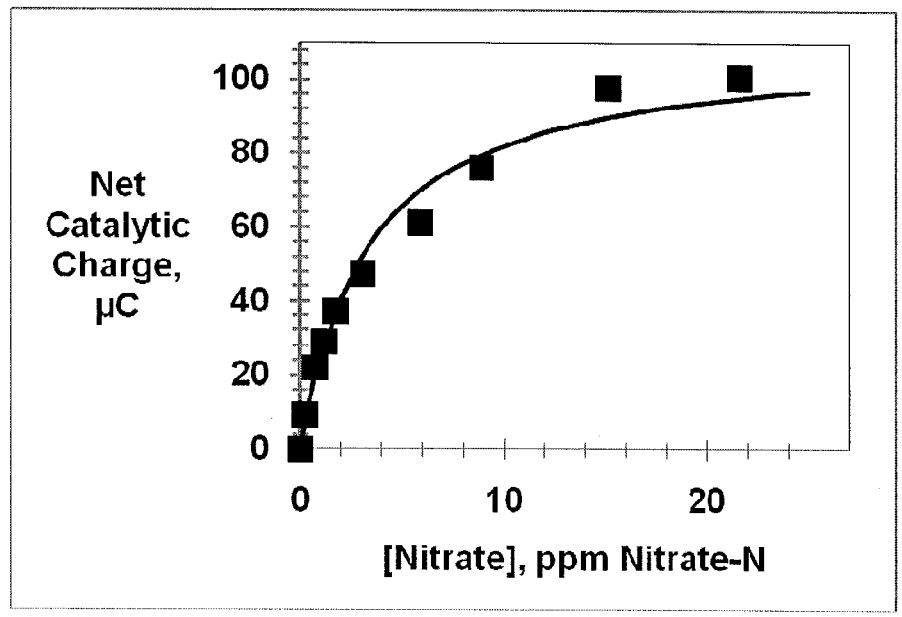

In applying Equation 4 to FIG. 10A data, y is observed catalytic current, x is the nitrate concentration, P1 is maximum catalytic current, and P2 is the nitrate concentration which yields one half the maximum catalytic current. In applying Equation 4 to FIG. 10B data, y is observed catalytic charge, x is the nitrate concentration, P1 is maximum catalytic charge, and P2 is the nitrate concentration which yields one half the maximum catalytic charge. The fit, by non-linear regression, to Equation 4 for FIG. 10A data yields a coefficient of correlation, $R^2$=0.99934; for analysis by maximum catalytic charge (FIG. 10B), $R^2$=0.99569. More specifically, FIG. 10A illustrates the increase in catalytic current with increasing [$NO_3^-$] in SPE at −1000 mV in 200 μL of 200 mM MOPS, pH 7.0, with 50 μM MV, 2.5 mM $KNO_3$, 20 μM EDTA, 50 mM glucose, glucose oxidase at 0.5 mg/mL, catalase at 0.5 mg/mL, and 1.2 units of YNaR1, after the potential is applied for 180 seconds. Ambient temperature=22° C. FIG. 10B depicts the increase in catalytic charge with increasing [$NO_3^-$] in SPE at −1000 mV in 200 μL of 200 mM MOPS, pH 7.0, with 50 μM MV, 2.5 mM $KNO_3$, 20 μM EDTA, 50 mM glucose, Glucose oxidase at 0.5 mg/mL, catalase at 0.5 mg/mL, and 1.2 units of YNaR1, after the potential is applied for 180 seconds. Ambient temperature=22° C.

In a third experiment, representative plant samples were used and their nitrate content measured with the reductase biosensor for nitrate model system. The samples are first measured in absence of NaR using a preset reaction time of 180 sec and a controlled potential of −1000 mV versus the reference electrode in the SPE. The background current and charge are then subtracted from the current and charge obtained for the plant sample, when measured in the presence of NaR, to obtain the net catalytic current and net accumulated catalytic charge. Next, the net catalytic current and net accumulated catalytic charge for each sample are compared to the respective standard curves for net catalytic current and net accumulated catalytic charge using Equation 4, to find the nitrate content of the plant samples. The results are shown in Table 1. The results of nitrate content found with the reductase biosensor for nitrate were compared to wet chemical determination of the nitrate content of the samples using an automated cadmium reduction analyzer and the Nitrate Test Kit from the Nitrate Elimination Co., Inc.

TABLE 1

Table 1 Nitrate Analysis of Plant Samples Comparing Wet Chemical Analysis versus Electrochemical Analysis with the Reductase Biosensor for Nitrate.

| | Nitrate Concentration (ppm Nitrate-N) | | | |
|---|---|---|---|---|
| Sample # | CdR Griess | AtNaR2 Griess | YNaR1 (current) electrochemical | YNaR1 (Charge) electrochemical |
| 2.2 | 1.61 | 1.75 | $1.70^a$ | $1.69^a$ |
| 1.3 | 2.36 | 2.28 | $2.11^a$ | $2.42^a$ |
| 1.11 | 3.96 | 3.83 | $4.00^a$ | $3.34^a$ |
| 1.11 | 3.96 | 3.83 | $4.81^b$ | $4.92^b$ |
| 1.10 | 4.18 | 4.26 | $4.04^b$ | $3.66^b$ |
| 2.18 | 1.22 | 1.17 | $1.23^b$ | $1.39^b$ |
| 2.21 | 1.21 | 1.52 | $1.58^b$ | $1.73^b$ |
| 1.40 | 1.18 | 1.19 | $0.96^b$ | $0.96^b$ |
| 1.17 | 3.65 | 4.00 | $3.37^b$ | $2.92^b$ |
| 1.30 | 4.36 | 4.90 | $4.48^b$ | $4.81^b$ |

Abbreviations:
CdR = cadmium reduction;
AtNaR2 = nitrate reductase based test kit; and
YNaR1 = Reductase Biosensor by either current or charge analysis applying the standard curves similar to those shown in FIG. 10.
Note:
In the wet chemical analysis methods, in other words CdR and AtNaR2, the Griess reagent is used to determine the nitrite content after reduction of the sample nitrate. Temperature = 22° C.
[a]sample was mixed with freeze dried buffer, MV, EDTA and glucose;
[b]pure sample solution added in equal volume to enzyme solution (with twice the concentration of buffer, MV, EDTA, glucose), each sample was measured twice.

Further experimental details, contemplations and examples are provided in our publication entitled "Enzyme-Catalyzed O(2) Removal System for Electrochemical Analysis under Ambient Air: Application in an Amperommetric Nitrate Biosensor" by Nicolas Plumeré, Jörg Henig, and Wilbur H. Campbell (Anal. Chem. 2012 Feb. 10; PMID: 22263529), which is incorporated by reference herein.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A method of reducing oxygen from an aqueous medium of an electrochemical process, comprising:
   combining in an aqueous medium an oxidase, an oxidase substrate, and a catalase to so form a test medium for use in an electrochemical process;
   wherein the oxidase produces from the oxidase substrate and dissolved oxygen in the test medium a reaction product and hydrogen peroxide;
   wherein at least one of the oxidase and the oxidase substrate is selected such that the reaction product maintains at least one of pH of the test medium, activity of an enzyme present in the electrochemical process, and reactivity of the reaction product in the electrochemical process over a predetermined test period;
   incubating the test medium for a time sufficient to deplete the test medium of dissolved oxygen while the test medium is exposed to ambient air; and
   performing the electrochemical process within the predetermined test period while the test medium is exposed to atmospheric oxygen.

2. The method of claim 1 wherein the test medium is a buffered aqueous medium.

3. The method of claim 1 wherein the test medium has a volume of equal or less than 1000 µL.

4. The method of claim 1 wherein the test medium has a ratio of surface to volume of at least 1 $cm^{-1}$.

5. The method of claim 1 wherein the electrochemical process comprises a reductase reaction.

6. The method of claim 5 wherein the reductase reaction is a nitrate reductase reaction.

7. The method of claim 1 wherein the electrochemical process comprises at least one of amperometry and coulometry.

8. The method of claim 1 wherein the oxidase is selected from the group consisting of an aldohexose oxidase, an amine oxidase, an amino acid oxidase, an aldehyde oxidase, and a urate oxidase.

9. The method of claim 1 wherein the step of incubating the test medium is performed in equal or less than 10 minutes.

10. The method of claim 1 wherein the predetermined test period is equal or less than 4 hours.

11. The method of claim 1 wherein the predetermined test period is equal or less than 1 hour.

12. The method of claim 1 wherein the step of performing the electrochemical process comprises reducing nitrate using a nitrate reductase and an electron transfer compound.

13. The method of claim 12 further comprising at least one of amperometry and coulometry.

14. The method of claim 12 wherein the oxidase is a pyranose oxidase, and wherein the oxidase substrate is glucose.

* * * * *